United States Patent [19]

Dixon

[11] Patent Number: 5,849,337

[45] Date of Patent: Dec. 15, 1998

[54] METHOD OF ENHANCING MAGNESIUM ABSORPTION AND PREVENTION OF ATHEROSCLEROSIS

[75] Inventor: Michael W. Dixon, Lake Forest, Calif.

[73] Assignee: Gusty Winds Corporation, Costa Mesa, Calif.

[21] Appl. No.: 883,287

[22] Filed: Jun. 27, 1997

[51] Int. Cl.$^6$ .......................... A01N 59/08; A61K 38/16; A61K 35/78; C07C 205/00
[52] U.S. Cl. .............................. 424/677; 424/681; 514/6; 530/370; 562/853
[58] Field of Search .................................. 514/2, 12, 13, 514/21, 6; 530/370; 424/677, 681; 562/553

[56] References Cited

U.S. PATENT DOCUMENTS 5,278,189  1/1994  Rath et al. ............................... 514/561
5,364,614  11/1994  Platzek et al. ............................. 424/9

*Primary Examiner*—José G. Dees
*Assistant Examiner*—Alton Pryor
*Attorney, Agent, or Firm*—Morland C. Fischer

[57] ABSTRACT

A method for making and administering a compounded coordination complex of magnesium that enhances the biological absorption of an effective amount of potentiated magnesium, and when administered in therapeutically effective dosages balances calcium metabolism, maintains the homeostasis of the cardiovascular system, and prevents atherosclerosis in the human body.

20 Claims, No Drawings

METHOD OF ENHANCING MAGNESIUM ABSORPTION AND PREVENTION OF ATHEROSCLEROSIS

BACKGROUND OF THE INVENTION

1. Field of the Invention

The present invention relates to a method of enhancing the biological absorption of an adequate quantity of the biochemically and physiologically important mineral salt magnesium and more particularly a method and compound that prevents atherosclerosis.

2. Background Art

Magnesium salts are essential in human nutrition. As part of adenosine triphosphate (ATP), magnesium is required for all biosynthetic processes, glycolysis, formation of cyclic adenosine monophosphate (cyclic AMP), is involved in energy metabolism and energy dependent membrane transport, and is required for ribonucleic acid (RNA) synthesis and transmission of the genetic code. Magnesium salts (a cation) are required for the activity of more than 300 enzymes (either by interaction between substrate and an active site or by induction of conformational change), and especially those enzymes concerned with oxidative phosphorylation. Magnesium salts are an important component of both intracellular and extracellular fluids. Intracellular magnesium is believed to control cellular metabolism by modulating the activity of rate limiting enzymes. Extracellular magnesium is critical to the maintenance of electrical potentials of nerve and muscle membranes and for transmission of impulses across neuromuscular junctions. Magnesium salts are important in maintaining the homeostasis of cardiac and smooth muscle tissues. In each of these physiological processes there is an interaction with the mineral salt calcium, which may act synergistically or antagonistically.

It is believed that there are 20 to 28 grams of magnesium in the adult human body. Approximately 59% is in the body's skeleton and bone structures, approximately 40% is in the body's musculature and soft body tissues, with approximately 1% (about 2 to 2.8 grams) in the body's extracellular fluid. Serum concentration ranges from 1.1 to 2.1 mEq./l in healthy individuals and is believed to be regulated primarily by the kidneys. Kidney filterable magnesium (serum magnesium not bound to protein) is either reabsorbed in the kidneys' proximal convoluted tubule or in Henle's loop, which is where major adjustments in response to serum concentrations are believed to take place. There is a passive equilibrium between a portion of skeletal magnesium and that in the blood which is believed to act as a modulator against fluctuations in extracellular magnesium concentrations.

Magnesium balances calcium and its functions within the human body. It is believed that the adult human body contains approximately 1200 grams of calcium, with approximately 99% of it in the skeleton, and approximately 1% (about 12 grams) in extracellular fluids, intracellular structures, and cell membranes. This approximately 1% plays an essential role, in conjunction with magnesium, in the functions of nerve conduction, muscle contraction, blood clotting, and membrane permeability. It is believed that serum calcium concentration is maintained by several hormones, including estrogen and testosterone. It is known that dietary protein enhances calcium absorption, and dietary phosphorus causes calcium retention.

Magnesium deficiency is known to cause nausea, muscle weakness, neuromuscular and cardiac irritability, tetany, convulsions, tremors, mental depression, psychotic behavior, inhibit proper muscle function and contractions, as well as interfere with the proper utilization of calcium and potassium.

Magnesium is inorganic and is not produced by the human body. Humans must rely upon dietary sources to provide the body with its magnesium requirements. Magnesium is a natural component of the earth's crust and finds its way into the diet of humans from the food products grown in soil. Foods containing the highest concentration of magnesium are unprocessed whole grains, legumes, and seeds. More than 80% of the magnesium content of unmilled grains are lost by removal of the germ portion and by the removal of the outer layer of the grains during the milling process. Diets rich in refined and processed foods, meats, and dairy products are low in magnesium content, in addition to increasing calcium absorption caused by protein consumption, and calcium retention caused by phosphorus consumption.

Dietary magnesium intake has declined in the United States, with a per capita decline of magnesium in the U.S. food supply (estimated as food flowing through the food distribution system) of from 408 mg./day in 1909 to 329 mg./day in 1986, almost a 20% decline. This is believed to be a relatively small decline when compared to many decades earlier when unrefined and unprocessed foods, along with a consumption of less meats and dairy products, were the dietary standard in the U.S. This closely correlates with the chemical analysis of typical U.S. diets in the Food and Drug Administration's Total Diet Study of 1976, 1977, 1980, 1981 and 1982, and with the United States Department of Agriculture's 1985 average magnesium intake of adult men, and the USDA's 1987 mean magnesium intake for adult women. The U.S. decline in dietary magnesium intake is directly attributable to the dietary decrease of unprocessed whole grains, legumes, and seeds, with a concurrent dietary increase of refined and processed foods, meats, and dairy products.

In those with normal digestion and assimilation, magnesium absorption from food is believed to be from approximately 40 to 60% of that ingested, with a slight reduction in absorption in the presence of phytate (a negatively charged form of phytic acid, i.e., inositol hexaphosphate found in plant leaves) or in the presence of fiber.

Magnesium depletion in humans can occur in those with inadequate dietary intake, excessive calcium intake, excessive or prolonged levels of stress, gastrointestinal tract abnormalities associated with malabsorption, renal reabsorption dysfunction, excessive fluid and electrolyte losses of systemic or diuretic drug causes, and by the interference of certain drugs.

Large oral intakes of magnesium are generally regarded as safe, with no evidence of harm in those with normal renal function. It is known that excessive oral intakes of magnesium may cause transitory diarrhea.

Oral intakes of magnesium are difficult for the body to absorb. It is believed that only 3 to 12% of elemental magnesium, typically in the form of magnesium oxide, is absorbed for use by the body. Past attempts to increase the amount of magnesium made available for absorption by the body have been only partially successful. These past attempts were concerned with chelating magnesium with protein amino acids or protein derivatives, such as hydrolyzed proteins, or more recently with free form amino acids. A magnesium chelate is where the mineral salt is covalently bound with a protein amino acid. These typically result in magnesium complexes of aspartate, citrate, fumarate, gluconate, ketoglutarate, succinate, taurinate, et al., or any combination thereof. Such a compound is commonly termed amino acid chelate, or just simply chelated. Some believe that the chelation of magnesium has resulted in an increase in the amount of magnesium made available for absorption by the body to almost equal the lower end of that which is believed to be absorbed from ingested food. This increase in absorption is believed by some to be approximately 37%, which may be more theoretical than actual, with studies suggesting that this percentage of absorption may be the maximum amount made available only under ideal conditions, i.e., with nothing otherwise interfering with its absorption, with actual amounts available for absorption believed to be closer to approximately 25% or less.

While there is evidence that magnesium chelated with protein amino acids is more effectively absorbed by the body, passing more efficiently through the intestinal cells into the blood than elemental magnesium, it is not completely clear how much more effective this is. Accordingly, there has been a degree of uncertainty attached to the selection of proper dosages of magnesium.

It is widely known that cardiovascular disease, which results in reduced arterial blood flow and can eventually manifest itself as heart attack, stroke, and peripheral arterial insufficiency, is the leading cause of death in the U.S. Past attempts at prevention of cardiovascular disease have generally been limited to dietary fat and cholesterol reduction, blood cholesterol lowering medications, and blood pressure lowering medications, all with less than 100% effectiveness and with sometimes substantial deleterious side effects. Recent past attempts at prevention of cardiovascular disease have included compounds which are believed to lower serum lipoprotein (a) and to inhibit the deposition of lipoprotein (a) in the arterial wall. This is more fully detailed in U.S. Pat. No. 5,278,189 to Matthias W. Rath, et al.

However, this approach can have significant side effects, and requires that those who it is administered to have their coagulation and fibrinolytic system regularly monitored and assessed. Long-term administration of lipoprotein (a) binding inhibitors require formulations in low dosages for safety reasons, which reduces the binding inhibitor's effectiveness. Further and importantly, long-term safety of such compounds in humans have not been proven. It is believed that some degree of cardiovascular disease prevention may be attributed to the lipoprotein (a) binding inhibitor compound, however it is clear that the basis for the compound's effectiveness, to whatever extent that might be, is believed to be the lipoprotein (a) binding inhibitor itself, as evidenced by its recommended use in cardiovascular disease treatment.

Moreover, and most importantly, no studies have been conducted to establish the effectiveness and safety of the long-term administration of the lipoprotein (a) binding inhibitor compound as a cardiovascular disease prevention in living humans, with previous research focusing on its use in lab animals and cadaver tissues. Furthermore, for optimization of the therapeutic effect of the lipoprotein (a) binding inhibitor compound, it is recommended that a time release composition be administered. Such a time release composition may be contraindicated in those with a compromised or sensitive gastrointestinal tract, which would have even more deleterious side effects and even less effectiveness.

Therefore, there exists a need for an improved form of magnesium which is more readily available for absorption by the human body and can be more precisely administered orally, and which has demonstrated long-term administration safety and atherosclerosis prevention qualities in the living human body.

SUMMARY OF THE INVENTION

Briefly, and in general terms, a method is disclosed for enhancing magnesium absorption by the human body when administered orally. This is accomplished by balancing in proper proportion the strong alkaline nature of inorganic magnesium salts with an acceptable, safe and compatible organic dietary acid resulting in a neutral pH, producing a potentiated magnesium compound, which allows for greater absorption, and when administered in effective amounts has the ability to balance calcium metabolism and to maintain the homeostasis of the cardiovascular system of the human body and prevent atherosclerosis.

In accordance with this discovery, it is an object of the invention to provide a composition and method for selectively administering the essential mineral salt magnesium in humans for facilitating absorption of this mineral salt composition by the intestinal cells and in magnesium utilization in conjunction with cellular metabolism.

It is also an object of the invention to administer a magnesium composition in a safe, physiological form that is readily acceptable by the body.

It is also an object of the invention to administer a magnesium composition which is well tolerated by the body.

It is another object of the invention to provide a magnesium composition which can be administered orally in a precise preselected manner.

It is another object of the invention to provide a magnesium composition, when administered in an effective amount, which can maintain the magnesium calcium balance in the human body.

It is another object of the invention to provide a magnesium composition, when administered in an effective amount, which can maintain the homeostasis of the body's cardiovascular system. The term "homeostasis" is used herein to distinguish the healthful balance, stabilization, and equilibrium of the body, its organisms, and its functions.

It is another object of the invention to provide a magnesium composition, when administered in an effective amount, which can reduce and normalize blood pressure.

It is another object of the invention to provide a magnesium composition, when administered in an effective amount, which can relieve and control cardiac arrhythmia extrasystole.

It is another object of the invention to provide a magnesium composition, when administered in an effective amount, which can prevent dystrophic calcification.

It is another object of the invention to provide a magnesium composition, when administered in an effective amount, which can prevent the formation of arterial plaque.

It is another object of the invention to provide a magnesium composition, when administered in an effective amount, which can prevent atherosclerosis. The term "atherosclerosis" is used herein to distinguish any form of cardiovascular disease, especially that which is characterized by arterial plaque formation, arterial constriction or spasm, thrombus formation, restricted or reduced arterial blood flow, or an increase in arterial blood pressure.

A further object of the invention is to provide a magnesium composition in a form which is simple to produce and economically feasible to distribute on a commercial basis.

Other objects and advantages of this invention will become readily apparent from the ensuing detailed description and the clinical case study.

DETAILED DESCRIPTION OF THE INVENTION

The term "potentiated magnesium" is used herein to distinguish the compound of the present invention. Potentiated magnesium is a compounded magnesium composition comprised of a coordination complex of magnesium, protein amino acids, and ascorbic acid in a ratio of 1:1:2, i.e., one part magnesium, one part protein amino acids, and two parts ascorbic acid, by weight. This composition of potentiated magnesium results in a balanced potential of hydrogen producing essentially a neutral pH factor (i.e., 0.0000001 gram atom of hydrogen ion per liter of solution—essentially the same pH of distilled water). When prepared in the indicated manner, the anionic ascorbic acid component acts as a strong complexing agent capable of binding the cationic magnesium component, effectively producing a ligand coordination complex. In addition, the second complexing with the ascorbic acid component reinforces the first complexing of the magnesium component with the protein amino acids allowing it to reach its full potential, with an exponential increase in its potential for intestinal cell absorption, cell utilization and effectiveness. This double complexing process can be thought of as a stepped double complexing or a compounded coordination complex. This compounded coordination complex effectively potentiates the magnesium producing a composition which is essentially 100% available for absorption by the intestinal cells resulting in maximum efficacy. Potentiated magnesium is an improvement over any other form of orally administered or ingested magnesium.

The potentiated magnesium compound is prepared by one of two methods: by adding two parts ascorbic acid to an aqueous solution of one part water soluble salt of magnesium complexed with one part protein amino acids, then recovered and dried by any conventional procedure; or simply, under ambient conditions, by completely blending two parts ascorbic acid with one part magnesium complexed with one part protein amino acids. The resulting compounded coordination complex magnesium composition is fully potentiated.

While the applicant does not wish to be bound to any particular theory, there appear to be at least ten mechanisms, or levels, at work that contribute to the effectiveness of potentiated magnesium: one is the double compounded complexing of magnesium; the second is the balancing of the potential of hydrogen of the compound; the third is the electrical anionic/cationic balance; the forth is the strong synergism of the coordination complexes' components; the fifth is the ratio of the coordination complexes' components; the sixth is the balancing of an inorganic dietary substance with an organic dietary substance; the seventh is the ability of the compound to balance calcium metabolism; the eighth is the compound's contribution to the homeostasis of the blood; the ninth is the compound's contribution to the homeostasis of the cardiac muscle and blood vessels; and the tenth is the compound's antioxidant benefit.

While the compound of the present invention is intended primarily for oral ingestion, it is envisioned that it may also be injected directly into the gastrointestinal tract or administered by parenteral application. When administered orally, it may be incorporated in foodstuffs as an enrichment, or it may be used alone as a powder, crystals or liquid. Alternatively, it may be manufactured into tablets, pills or capsules with any suitable binder or carrier using any known technique.

Because the compound of the present invention is substantially 100% available for absorption by the body's intestinal cells, administration may be more precisely controlled and limited to physiological amounts that satisfy the requirement. This provides an important advantage of potentiated magnesium in that it permits precise, preselected control over the amount of consumption to fit the need.

Because of the balancing properties of potentiated magnesium, it can be administered orally with foodstuffs or with other nutrients without interference of either, or can be administered on an empty stomach without gastric upset, and without any reduced effectiveness. It appears to be well tolerated, even by those with certain types of systemic absorption difficulties, such as irritable bowel syndrome (IBS), in whom delayed or sustained release (also known as timed release) preparations can cause sometimes severe intestinal tract irritation.

Another major advantage of potentiated magnesium is the complimentary aspect of its ascorbic acid component. In addition to it balancing and assisting magnesium, some of its functions and benefits are very similar to those of magnesium, not the least of which is ascorbic acid's function with numerous enzymes, and its beneficial role in maintaining the homeostasis of smooth muscle tissues. Likewise, magnesium also compliments ascorbic acid by modulating the possible formation of oxalate crystals, i.e., calcium oxalate renal calculi. This synergism is a strong indicator of the likely mechanism of the compound's exponential efficacy. Like magnesium, ascorbic acid is generally regarded as safe, even with large intakes, in those with normal renal function.

In accordance with the present invention, and as will be demonstrated below, an unexpected discovery and benefit from the administration of potentiated magnesium is to provide a protective advantage for the cardiovascular system by preventing atherosclerosis. Potentiated magnesium provides a distinct improvement over any other form of orally administered cardiovascular disease prevention preparation. Its effectiveness and safety in the living human body have been shown, as will be clearly detailed in the clinical case study below.

The following examples are only to further illustrate the present invention and are not intended to limit the true spirit or scope of the invention.

EXAMPLE 1

In a nonreactive glass vessel, 500 mg. magnesium chloride (USP) complexed in equal proportion with amino acids from vegetable protein was dissolved in 100 ml. distilled water at room temperature. Thereafter, 1000 mg. ascorbic acid (USP), of vegetable source, was added to the solution and the solution was stirred continuously. The glass vessel containing the solution was placed into a heating vessel. Then water was added to the heating vessel to just above the height of the solution, with the solution within the glass vessel and the water in the heating vessel never coming into contact. The heating vessel water was then heated to a boil, while the solution within the glass vessel was stirred continuously. Without bringing the solution to boil, the solution was heated and stirred until the mixture of the solution had completely dissolved, after which the glass vessel was submerged in an ice bath and then stored in a refrigerated compartment for 24 hours. After 24 hours the crystals were separated and freeze dried. Assay of the crystals showed that the coordination complex conversion of potentiated magnesium contained approximately 425 mg. complexed magnesium and 848 mg. ascorbic acid with a neutral pH of 7.0.

EXAMPLE 2

The procedure of Example 1 was repeated except that the heated solution was dried in a steam heated dryer instead of the cooling, crystallization and freeze drying steps. Assay of the product showed essentially the same results of Example 1.

EXAMPLE 3

The procedure of Example 1 was repeated except that the amount of distilled water used was reduced to 5 ml. and the heated solution was warm air dried instead of the cooling, crystallization and freeze drying steps. Assay of the product showed essentially the same results of Example 1.

EXAMPLE 4

A solution was prepared by dissolving in a nonreactive glass vessel 500 mg. magnesium chloride (USP) complexed in equal proportion with amino acids from vegetable protein, and 1000 mg. ascorbic acid (USP) of vegetable source, in 5 ml. distilled water at room temperature, as the mixture solution was stirred continuously. The aqueous mixture solution was not heated, and the product was air dried. Assay of the product showed the coordination complex conversion of potentiated magnesium was approximately 100%, which showed approximately 500 mg. complexed magnesium and 1000 mg. ascorbic acid.

EXAMPLE 5

A compound was prepared by completely blending 500 mg. magnesium oxide (USP) complexed in equal proportion with amino acids from vegetable protein, and 1000 mg. ascorbic acid (USP) of vegetable source. The mixture was not prepared in an aqueous solution, and, as a result, there was no drying requirement. Assay of the product showed the coordination complex conversion of potentiated magnesium was approximately 100%, which showed 500 mg. complexed magnesium and 1000 mg. ascorbic acid.

CLINICAL CASE STUDY

The course of a human male subject, from age 26 to age 52, was closely reviewed and evaluated.

The subject has a strong family history of atherosclerosis in virtually all blood related family members. His father experienced ongoing cardiac arrhythmia and had a pacemaker implant, had two extensive femoral bilateral bypasses as a result of extensive atherosclerosis, and had suffered two strokes before dying at age 78. His mother died at age 66 from a heart attack while suffering from inoperable cancer. On his father's side of the family, the subject's uncle, his father's younger and only brother, also had a pacemaker implant, had triple heart bypass surgery, and had suffered a stroke. This uncle's only son, the subject's cousin, who is 4 years younger than the subject, has atherosclerosis. The subject's aunt, his father's older sister, and her only son, the subject's cousin who is 8 years older than the subject, both have extensive atherosclerosis. The subject's grandmother, his father's mother, died at age 28 from a heart attack. On his mother's side of the family, his aunt, his mother's younger sister, had triple heart bypass surgery. His uncle, his mother's older brother, had quadruple heart bypass surgery. His cousin, his mother's brother's son, who is 6 years older than the subject, has had two triple heart bypass surgeries.

The subject has two younger sisters and no brothers. One sister is 4 years younger than the subject and the other sister is 7 years younger. Both sisters have atherosclerosis. The subject's son, now age 30, has suffered from cardiac arrhythmia extrasystole since age 26. The subject smoked two packs of cigarettes for seven years, but quit smoking three years before experiencing any symptomatology. The subject consumed an average diet principally high in dietary fat, estimated to be at least 40% of the calories consumed. The subject exercised regularly on a moderate basis when younger but became sedentary as he got older. The subject was in a particularly high stress profession for a period of 10 years, from age 29 through age 39, during which time chronic irritable bowel syndrome (IBS) was misdiagnosed at age 33 as colitis. This was later correctly diagnosed as chronic IBS at the age of 43. The subject has an intense personality, the so-called Type A personality. For stress management the subject engaged in biofeedback training, self-hypnosis, and training in the Relaxation Response, all with varying degrees of failure, although some stress reduction was noted with regular physical exercise.

At age 26, the subject experienced symptoms of magnesium deficiency, i.e., muscle weakness, neuromuscular irritability, and ongoing cardiac arrhythmia in the form of extrasystole, thought to be premature ventricular contractions (PVCs). A complete medical workup at the time, including electrocardiograms, echocardiograms, a Holter monitor, a treadmill stress test, an angiogram, and neurologic evaluation, ruled out other possibilities.

At the time of symptomatology onset the subject had been consuming calcium of about 1200 mg./day in the form of bone meal tablets. The calcium was discontinued, and magnesium was administered in the form of magnesium oxide tablets. Some slight improvement occurred but only at high levels of consumption of the magnesium oxide tablets of about 1500 mg./day. Such high levels of consumption of magnesium oxide tablets tended to cause transitory diarrhea in the subject, which exacerbated his condition of chronic IBS. Occasionally it was observed by the subject that some of the magnesium oxide tablets would pass through his body essentially intact. It is believed this occurred as a result of the difficult absorption nature of magnesium oxide, combined with the subject being especially sensitive as a result of his IBS condition. With the subject's sensitive intestinal tract, the difficult absorption nature of magnesium, and the subject's requirement for effective magnesium administration, the subject became the perfect test subject for establishing a more effectively absorbed magnesium compound. In addition to the magnesium requirement, the subject had an increased requirement for ascorbic acid intake to control a problem with bleeding gums. After the subject had been taking magnesium oxide and the increased ascorbic acid intake, it was later discovered that when magnesium oxide was taken with ascorbic acid it tended to increase magnesium's absorption, with a secondary benefit of modulating the irritating acidity nature of ascorbic acid with the alkaline nature of magnesium. Through experimentation it was determined that the optimum ratio of magnesium to ascorbic acid appeared to be 1 to 2.

Although an improved method of magnesium absorption had been discovered, the amount of magnesium absorption improvement was not significant because of the less than optimal nature of magnesium oxide. With daily consumption of prescribed psyllium hydrophilic mucilloid fiber controlling the IBS, which resulted in a less sensitive intestinal tract, a more effective magnesium compound was sought. With the availability of chelated magnesium (amino acid chelate) came another slight increase in effectiveness, but still some symptoms persisted. Then, in an effort to improve the effectiveness of chelated magnesium, the composition of the present invention was developed.

In this regard, the composition of Example 5 was administered to the subject, which ended all symptoms, and was well tolerated. This was followed by administering the composition of Example 4, in the same amount, with there being no difference noted in its effects than that of the composition of Example 5. All symptoms ended. Both the compositions of Examples 4 and 5 were very well tolerated, which was tested by the subject's intestinal sensitivity level when psyllium fiber was discontinued for a period of time sufficient to make that determination. The effectiveness of the compositions of Examples 4 and 5 were tested numerous times by noting the return of the symptoms, most notably cardiac arrhythmia extrasystole, when the preparations were discontinued, and it was noted that the subject became completely asymptomatic with the resumption of the preparations. Further, the subject's son also controlled his cardiac arrhythmia extrasystole with the same preparations. With the subject having taken no medications of any kind, it was noted that nothing else ingested or in lifestyle was extraordinary which could otherwise account for the observed beneficial effects produced by the compositions of Examples 4 and 5.

The increases in the absorption level of magnesium in the subject are delineated in Table 1.

TABLE 1

Serum Magnesium Levels

| | |
|---|---|
| No Magnesium Administered | 1.0 mEg./l |
| Magnesium Oxide | 1.1 mEq./l |
| Magnesium Oxide w/Ascorbic Acid | 1.3 mEq./l |
| Chelated Magnesium | 1.4 mEq./l |
| Potentiated Magnesium | 1.7 to 1.9 mEq./l |

As shown in Table 1, potentiated magnesium has a significantly higher level of absorption in the subject than any other magnesium preparation, with it consistently showing a serum level 26% higher than chelated magnesium, 32% higher than magnesium oxide with ascorbic acid, 42% higher than elemental magnesium oxide, and 47% higher when no magnesium is administered in the subject.

Table 2 delineates the quantity of magnesium administered to the subject, which correlates with the serum magnesium levels of Table 1.

TABLE 2

Magnesium Administered

| | |
|---|---|
| No Magnesium Administered | 0 |
| Magnesium Oxide | 1500 mg./day |
| Magnesium Oxide w/Ascorbic Acid | 1500 mg./day |
| Chelated Magnesium | 1500 mg./day |
| Potentiated Magnesium | 1500 mg./day |

Except for potentiated magnesium, all amounts administered to the subject, as shown in Table 2, are the upper limit of each of those preparations which could be tolerated by the subject. The upper limit of potentiated magnesium which could be tolerated by the subject was approximately 2250 to 2500 mg./day, an increase of 33 to 40%. All preparations shown in Table 2 were administered in two evenly divided dosages of 750 mg. each of magnesium, twice a day, once in the morning and once in the evening, approximately 12 hours apart, usually immediately following a meal. It was noted that the potentiated magnesium compound, and to a somewhat lesser extent, the magnesium oxide taken with ascorbic acid, were better tolerated by the subject's sensitive intestinal tract than both the chelated magnesium or the magnesium oxide alone. The potentiated magnesium was so well tolerated by the subject that it could be taken on an empty stomach with no side effects or discernable discomfort. It was further noted that the potentiated magnesium could be administered in larger dosages than any of the other magnesium preparations before the telltale sign of magnesium overconsumption (transitory diarrhea) would occur, further indicating the higher absorption ability of potentiated magnesium. It has been noted and well documented that the subject has been administered the potentiated magnesium compound and as a result has experienced no adverse or deleterious side effects of any kind. The potentiated magnesium compound appears to be completely and 100% safe to administer, as long as those it is administered to have normal renal function.

At the age of 52, the subject requested a complete medical workup because of his concern over the subject's strong family history of atherosclerosis and the likelihood of this manifesting its deleterious effects as he got older. A complete workup was conducted, including an extensive Doppler ultrasound of the subject's entire cardioarterial system, especially concentrating on the bifurcation of the carotid arteries, the cardiac arteries, and the femoral arteries. The unexpected result of the workup revealed no arterial plaque formations anywhere throughout the subject's cardioarterial system. The findings were independently confirmed by the supervising doctor during the Doppler ultrasound procedure. The findings were unexpected due to the subject's strong family history of atherosclerosis, the subject's age at workup, his poor dietary habits, his sedentary lifestyle, his intense personality, his high stress level, and his high blood cholesterol. What was perplexing was the lack of correlation of the findings with the subject's high blood cholesterol profile (the subject was not administered cholesterol lowering medication at anytime).

The subject's blood cholesterol levels are shown in Table 3.

TABLE 3

Serum Cholesterol Levels

| | |
|---|---|
| Total Cholesterol | 241 to 293 mg./dl |
| HDL Cholesterol | 50 to 70 mg./dl* |
| LDL Cholesterol | 148 to 200 mg./dl |
| Triglycerides | 49 to 165 mg./dl |

*One serum sample showed a HDL Cholesterol level of 92 mg./dl.

By all accounts, this 52 year old male subject should have had some degree of atherosclerosis—but none was detected. In close evaluation of the subject it was observed that the only extraordinary aspects about the subject was the fact that he had no evidence of atherosclerosis, and he had been taking the potentiated magnesium composition.

It was noted that the subject's blood pressure readings before beginning the potentiated magnesium regimen was consistently about 140 mm. Hg systolic and 90 mm. Hg diastolic (140/90), and was sometimes as high as 150/100. The subject was not administered blood pressure lowering medication at anytime. It was noted that after the subject began the potentiated magnesium regimen the subject's blood pressure was consistently about 130/73, and sometimes as low as 128/68. As there were no other influences which could have accounted for this reduction of the subject's blood pressure, it is believed this occurred as a direct result of the potentiated magnesium regimen of the subject. It is well known that magnesium has a relaxing effect on the body's muscles. This includes the body's cardiac muscle tissues and smooth muscle tissues, i.e., the heart and blood vessels.

Accordingly, it has now been discovered that potentiated magnesium is absorbed more effectively by the human body, and when administered in an effective amount, has a profoundly beneficial influence on the homeostasis of the body's cardiovascular system, and that potentiated magnesium has the ability to reduce and normalize the blood pressure, relieve and control cardiac arrhythmia extrasystole, and to prevent atherosclerosis.

The likely mechanisms responsible for the beneficial effects observed as a result of administering the potentiated magnesium composition are the interaction of the composition with calcium on several different but related levels, the arterial strengthening and elasticity support provided by the composition, the free radical damage prevention qualities of the composition, and the unusually complimentary synergism of the compound's components with its exponential increase of effects in vivo.

Impairment of calcium metabolism, thought to be caused by free radical damage, allows excessive calcium to enter cells resulting in damage and malfunction. It is known that calcium activates phospholipase-A, which cleaves arachidonic acid from membrane phospholipids. Arachidonic acid produces prostaglandin and leukotrienes, which create free radicals. The inflammatory substances leukotrienes attract and stimulate leukocytes, which produce superoxide free radicals during phagocytosis causing free radical damage to surrounding tissues. Damaged blood vessel arterioles and capillaries dilate causing edema and erythrocyte leakage through the blood vessel walls. Microthrombi is produced by stimulated platelets, while erythrocytes release free iron and copper which causes an increase of tissue damage. Excessive calcium in smooth muscle cells (i.e., blood vessel cells), as a result of free radical damage to the cells, is bound to calmodulin activating myosin kinase, which phosphorylated myosin causing myosin and actin to constrict producing muscle cell contraction. The same thing occurs in cardiac muscle cells. Increased calcium within muscle cells can cause muscle spasm. When constriction occurs in the smooth muscle fibers of the blood vessels, blood flow is reduced and blood pressure is increased. When constriction occurs in the cardiac muscle fibers of the heart, angina or even myocardial infarction can occur. It is known that excessive intracellular calcium impairs myocardial function by reducing oxygen utilization efficiency. Intracellular calcium excess also results from increased ionized serum calcium levels which slowly increase with age, partially as a result of excessive dietary phosphates, making it more difficult to prevent excessive calcium from entering cells. Stress, another factor, causes retention of cellular calcium as a result of stress increased circulating catecholamines, which lessens the integrity of magnesium calcium ATPase. When metabolized, catecholamines produce free radicals. Free radicals have been implicated in atherosclerosis.

Magnesium is a natural calcium channel blocker that inhibits the entry of calcium into cells and inhibits the mobilization of calcium from intracellular stores, resulting in slowing of atrioventricular and sinoatrial conduction and relaxation of arterial smooth and cardiac muscle. This accounts for both the elimination of extrasystole and the blood pressure lowering and normalizing effect seen in the subject. Magnesium counters the effects of calcium induced stress. It is believed that a complex sequence of events which result in free radical damage, along with stress, are the basis for atherosclerosis. The improper utilization of calcium appears to be at least part of the atherosclerosis equation. Potentiated magnesium helps stabilize and balance calcium metabolism, thus normalizing its functions.

It is well known that one of the components of arterial plaque is calcium. Although it is known that calcification of arterial plaque occurs in the late stages of plaque formation, regular high serum levels of magnesium, as provided by potentiated magnesium, are believed to help prevent plaque calcification by balancing and normalizing serum calcium's functions. Although magnesium has a known antagonistic quality with calcium, it does not use up or eliminate calcium but rather balances its functions. This was evidenced by the subject's monitored serum calcium levels during the potentiated magnesium regimen, which consistently remained within normal ranges from 8.8 to 9.9 mg./dl, without any calcium being administered. It is believed that administered calcium may exacerbate unbalanced calcium and its detrimental effects.

It is well known that ascorbic acid maintains the homeostasis of the body's collagenous structures, such as the blood vessels. A clinical deficiency in ascorbic acid leads to the serious condition of scurvy, which is characterized by the weakening of the blood vessels resulting in widespread capillary hemorrhaging. It is believed that a subclinical deficiency in ascorbic acid, especially of long duration, still weakens the blood vessels but less severely than a clinical deficiency. Because of the generally weakened nature of the blood vessels, a subclinical deficiency may manifest itself as bleeding gums or as very small blood vessel hemorrhages. As the body repairs the very small hemorrhages, the natural repair materials and functions, such as the formation of intrinsic and extrinsic prothrombin and thrombin and then the formation of stable fibrin polymers, contribute to atherosclerosis. It is believed that regularly administered potentiated magnesium prevents these conditions because of the effects of its ascorbic acid component and because of the compound's unusually strong magnesium synergy resulting in making the ascorbic acid component even more effective. It is also believed that because of the nature of the ascorbic acid component being a strong antioxidant, it further contributes to the prevention of atherosclerosis as a result of its ability to protect the body from free radical damage, which is thought by many to be the root cause of atherosclerosis. Generally, administered potentiated magnesium can be thought of as producing a normalizing effect on the blood, the heart, and on the blood vessels, obvious complimentary functions.

The conclusions reached as a result of the analysis of the clinical case study are listed below.

1. Potentiated magnesium is absorbed more effectively than any other orally administered form of magnesium.
2. Potentiated magnesium provides more useable magnesium for use by the body than any other orally administered form of magnesium.
3. Potentiated magnesium is well tolerated, not producing gastric upset or intestinal irritability, even in those with compromised or sensitive gastrointestinal tracts.
4. Potentiated magnesium is safe, and has no deleterious side effects in those with normal renal function.
5. Potentiated magnesium can effectively balance calcium metabolism, and can do so without any serum calcium sacrifice.
6. Potentiated magnesium can effectively reduce and normalize blood pressure.
7. Potentiated magnesium can effectively relieve and control certain types of cardiac arrhythmia extrasystole.
8. Potentiated magnesium can effectively prevent dystrophic calcification.

9. Potentiated magnesium can effectively prevent the formation of arterial plaque.
10. Potentiated magnesium may prevent cardioarterial constriction and spasm.
11. Potentiated magnesium may inhibit thrombus formation or inhibit thrombus size increase by lessening serum calcium's role in clotting.
12. Potentiated magnesium provides a balance, maintains the integrity, and tends to normalize the cardiovascular system by maintaining the homeostasis of the blood, the heart, and the blood vessels.
13. Potentiated magnesium has a natural strong synergism between its components that results in an exponential increase in its effectiveness in vivo.
14. One of the causes of atherosclerosis may be the body's reaction to longstanding insufficient quantities of effective amounts of readily absorbable magnesium and ascorbic acid not being available in the body to prevent cell damage, arterial weakening, and free radical damage caused by unbalanced calcium.
15. Whereas adequate amounts of magnesium beneficially affect the blood, the cells, and the neuromuscular tissues of the cardiovascular system, and adequate amounts of ascorbic acid beneficially affect the blood and the blood vessel structures, when protein amino acid complexed magnesium and ascorbic acid are compounded together to form a compounded coordination complex of potentiated magnesium there is an exponential increase in effectiveness and when administered in effective amounts prevents atherosclerosis.

It will be apparent that while a preferred embodiment of the invention has been described, various modifications and variations may be made therein without departing from the true spirit and scope of the invention. In that regard, it should be recognized that the potentiated magnesium compound disclosed herein may include any pharmaceutically acceptable magnesium, protein amino acids, and ascorbic acid, and may contain different proportions of each which are suitable for the purposes described herein. Therefore, the particular ratio of ingredients listed above are for purposes of example and are not intended to be a limitation of the invention.

Having described my invention in such terms as to enable those skilled in the art to understand and practice it, and having identified the presently preferred embodiments thereof, what is claimed is:

1. A method for making a compounded coordination complex of magnesium administered in an amount that is effective to enhance the absorption of magnesium by the human body, said method comprising the steps of complexing magnesium with protein amino acids to form a coordination complex, and complexing said coordination complex with ascorbic acid so as to fully potentiate said magnesium.

2. The method recited in claim 1, including the additional steps of complexing said magnesium with said protein amino acids in equal amounts by weight to form said coordination complex, and complexing said coordination complex with said ascorbic acid in equal amounts by weight to form said compounded coordination complex.

3. The method recited in claim 1, including the additional step of selecting said magnesium from a group consisting of pharmaceutically acceptable magnesium, its salts and mixtures thereof.

4. The method recited in claim 1, including the additional step of selecting said ascorbic acid from a group consisting of pharmaceutically acceptable ascorbic acid, its salts and mixtures thereof.

5. The method recited in claim 1, wherein said compounded coordination complex of magnesium is administered orally.

6. The method recited in claim 1, wherein said compounded coordination complex of magnesium is administered by parenteral application.

7. A method for making a compounded coordination complex of magnesium administered in an amount that is effective to reduce and normalize blood pressure in the human body, said method comprising the steps of complexing magnesium with protein amino acids to form a coordination complex, and complexing said coordination complex with ascorbic acid so as to fully potentiate said magnesium.

8. The method recited in claim 7, including the additional steps of complexing said magnesium with said protein amino acids in equal amounts by weight to form said coordination complex, and complexing said coordination complex with said ascorbic acid in equal amounts by weight to form said compounded coordination complex.

9. A method for making a compounded coordination complex of magnesium administered in an amount that is effective to relieve and control cardiac arrhythmia extrasystole in the human body, said method comprising the steps of complexing magnesium with protein amino acids to form a coordination complex, and complexing said coordination complex with ascorbic acid so as to fully potentiate said magnesium.

10. The method recited in claim 9, including the additional steps of complexing said magnesium with said protein amino acids in equal amounts by weight to form said coordination complex, and complexing said coordination complex with said ascorbic acid in equal amounts by weight to form said compounded coordination complex.

11. A method for making a compounded coordination complex of magnesium administered in an amount that is effective to prevent dystrophic calcification in the human body, said method comprising the steps of complexing magnesium with protein amino acids to form a coordination complex, and complexing said coordination complex with ascorbic acid so as to fully potentiate said magnesium.

12. The method recited in claim 11, including the additional steps of complexing said magnesium with said protein amino acids in equal amounts by weight to form said coordination complex, and complexing said coordination complex with said ascorbic acid in equal amounts by weight to form said compounded coordination complex.

13. A method for making a compounded coordination complex of magnesium administered in an amount that is effective to prevent the formation of arterial plaque in the human body, said method comprising the steps of complexing magnesium with protein amino acids to form a coordination complex, and complexing said coordination complex with ascorbic acid so as to fully potentiate said magnesium.

14. The method recited in claim 13, including the additional steps of complexing said magnesium with said protein amino acids in equal amounts by weight to form said coordination complex, and complexing said coordination complex with said ascorbic acid in equal amounts by weight to form said compounded coordination complex.

15. A method for making a compounded coordination complex of magnesium administered in an amount that is effective to prevent atherosclerosis in the human body, said method comprising the steps of complexing magnesium with protein amino acids to form a coordination complex, and complexing said coordination complex with ascorbic acid so as to fully potentiate said magnesium.

16. The method recited in claim 15, including the additional steps of complexing said magnesium with said protein amino acids in equal amounts by weight to form said coordination complex, and complexing said coordination complex with said ascorbic acid in equal amounts by weight to form said compounded coordination complex.

17. A method for making a compounded coordination complex of magnesium administered in an amount that is effective to balance calcium metabolism in the human body, said method comprising the steps of complexing magnesium with protein amino acids to form a coordination complex, and complexing said coordination complex with ascorbic acid so as to fully potentiate said magnesium.

18. The method recited in claim 17, including the additional steps of complexing said magnesium with said protein amino acids in equal amounts by weight to form said coordination complex, and complexing said coordination complex with said ascorbic acid in equal amounts by weight to form said compounded coordination complex.

19. A method for making a compounded coordination complex of magnesium administered in an amount that is effective to maintain the homeostasis of the cardiovascular system of the human body, said method comprising the steps of complexing magnesium with protein amino acids to form a coordination complex, and complexing said coordination complex with ascorbic acid so as to fully potentiate said magnesium.

20. The method recited in claim 19, including the additional steps of complexing said magnesium with said protein amino acids in equal amounts by weight to form said coordination complex, and complexing said coordination complex with said ascorbic acid in equal amounts by weight to form said compounded coordination complex.

* * * * *